United States Patent [19]

Plotkin

[11] Patent Number: 5,738,645
[45] Date of Patent: Apr. 14, 1998

[54] SOFT TIP BLOOD RESERVOIR FOR HEART-LUNG MACHINES

[75] Inventor: Neil D. Plotkin, Pasadena, Calif.

[73] Assignee: Medtronic, Inc., Minneapolis, Minn.

[21] Appl. No.: 643,147

[22] Filed: Apr. 30, 1996

[51] Int. Cl.⁶ .................................................. A61M 37/00
[52] U.S. Cl. ............................................. 604/4; 604/410
[58] Field of Search .............................. 604/4–6, 408, 604/410; 422/44–48

[56] References Cited

U.S. PATENT DOCUMENTS

| | | |
|---|---|---|
| 4,474,568 | 10/1984 | Schoendorfer et al. ............... 604/4 |
| 4,622,032 | 11/1986 | Katsura et al. ...................... 604/4 |
| 4,642,089 | 2/1987 | Zupkas et al. ....................... 604/4 |
| 4,976,707 | 12/1990 | Bodicky et al. ...................... 604/4 |
| 4,976,708 | 12/1990 | Oshiyama ........................... 640/4 |
| 5,049,146 | 9/1991 | Bringham et al. .................... 604/4 |
| 5,270,005 | 12/1993 | Raible ............................... 604/4 |

Primary Examiner—John G. Weiss
Assistant Examiner—Ki Yong O
Attorney, Agent, or Firm—Harry G. Weissenberger

[57] ABSTRACT

In a venous/cardiotomy reservoir, substantially accurate volume indication and post-operative use are provided while preventing introduction of air into the reservoir outlet, by interposing a collapsible bag between the underside of a rigid reservoir housing and the reservoir outlet.

6 Claims, 2 Drawing Sheets

SOFT TIP BLOOD RESERVOIR FOR HEART-LUNG MACHINES

FIELD OF THE INVENTION

This invention relates to blood reservoirs for use in heart-lung machines, and more particularly to a soft-tipped reservoir which automatically shuts down the cardiopulmonary circuit as a safety measure if the liquid in the reservoir is exhausted.

BACKGROUND OF THE INVENTION

In open-heart surgery, a heart-lung machine is conventionally used to circulate and oxygenate the patient's blood while the heart is stopped. The heart-lung machine conventionally includes a venous reservoir which acts as a buffer in the extracorporeal cardiopulmonary circuit by storing blood diverted from the patient's circulatory system until it is pumped back into the patient's circulatory system through an oxygenator.

Because a significant amount of blood spills into the chest cavity during open-heart surgery, the venous reservoir is often combined with a cardiotomy filter and defoaming assembly. This assembly filters and defoams blood sucked from the chest cavity by a suction pump and returns it to the cardiopulmonary circuit by feeding it into the venous reservoir.

The operator of the heart-lung machine, also called a perfusionist, must maintain a level in the venous/cardiotomy reservoir such that air is not pumped into the patient's circulatory system where it would cause great physical harm. Hence, one function of the reservoir is to act as a liquid seal against the intrusion of air into the lines. Another function is to act as an air-liquid separator for the cardiotomy blood suctioned from the surgical field.

Another duty of the perfusionist is to manage both the overall volume and distribution of the blood between the patient and bypass circuit. Since the patient's blood is commonly diluted to a significant extent in bypass surgery, the reservoir provides a space for the extra fluid volume, a means for adjusting the fluid volume inside and outside of the patient, and a means of measurement of the quantity of fluid outside of the body. Consequently, the reservoir must be capable of continuously indicating the volume of blood in the reservoir.

Venous reservoirs are currently commercially available in two basic varieties: hard shell and soft bag. The hard shell reservoir is composed of a rigid molded plastic bucket, molded lid and often a filter/defoamer assembly to process the blood suctioned from the surgical field. Hard shell reservoirs typically have capacity for three to four liters of fluid. The rigid container allows the placement of markings denoting the volumetric level in the reservoir with sufficient accuracy for utility in the clinical environment. The hard shell reservoir is typically run as an open (vented to the atmosphere) system. One drawback of the hard shell reservoir is that the perfusionist must continually monitor the liquid level to prevent complete draining and subsequent pumping of air into the patient.

Soft bag reservoirs are typically composed of sheets of flexible PVC (polyvinyl chloride) film sealed around the edges to form a bag. Soft bags are typically run as a closed (non-vented) system. As the volume in the bag decreases, the bag collapses on itself. Since there is little or no air normally in the system it is more difficult to pump air in the event of completely draining the bag. Some crude filtration/defoaming capability is incorporated into the soft bag but generally a separate cardiotomy reservoir is employed to handle the filtration, defoaming, and air-liquid separation tasks for suctioned blood.

The capacity of the soft reservoir bags is typically less than two liters. In order for the bag to be able to freely collapse when emptied, the opposing walls must be in reasonably close proximity and relatively parallel to one another. This forces the bag shape to be relatively tall and thin and a large external support frame is required to maintain the soft bag in an upright position. Since the volume of the bag is variable, the accuracy of any volumetric markings depends on the shape of the bag as positioned in the support frame. In general, the perfusionist must crudely estimate the volume of blood in a soft reservoir.

SUMMARY OF THE INVENTION

The present invention overcomes the above-described deficiencies of the prior art by providing a reservoir consisting of a rigid plastic container with a truncated snout to which a soft flexible PVC film outlet section is attached, a rigid plastic lid, and a filter-defoamer assembly. This configuration provides the large capacity, air handling, and filtration/defoaming capability of a rigid reservoir along with the collapsible walls and air bohs retardation of a soft bag reservoir, yet substantially retains the volumetric accuracy of a rigid reservoir.

DESCRIPTION OF THE PREFERRED EMBODIMENT

Figure 1:
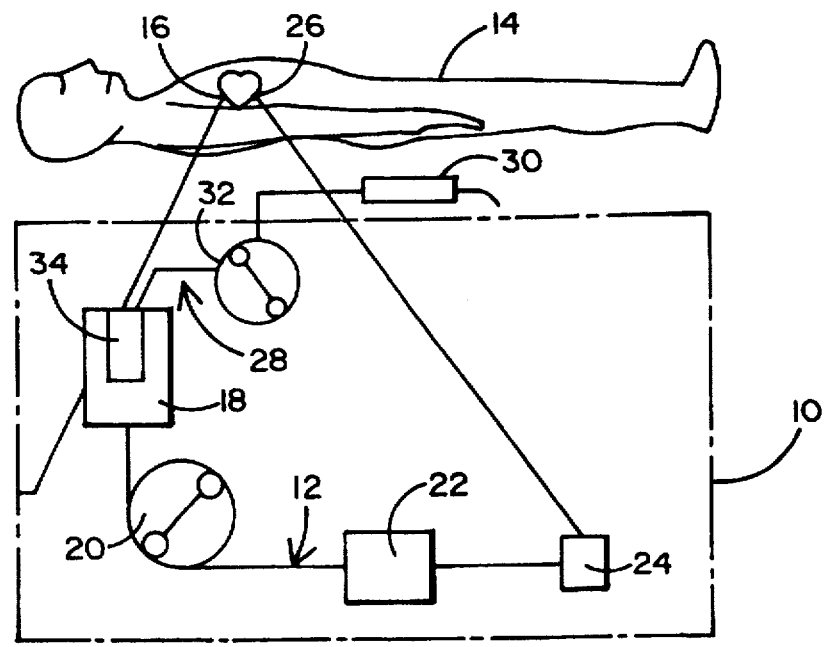
FIG. 1 schematically shows a conventional cardiopulmonary/cardiotomy circuit.
Figure 2:
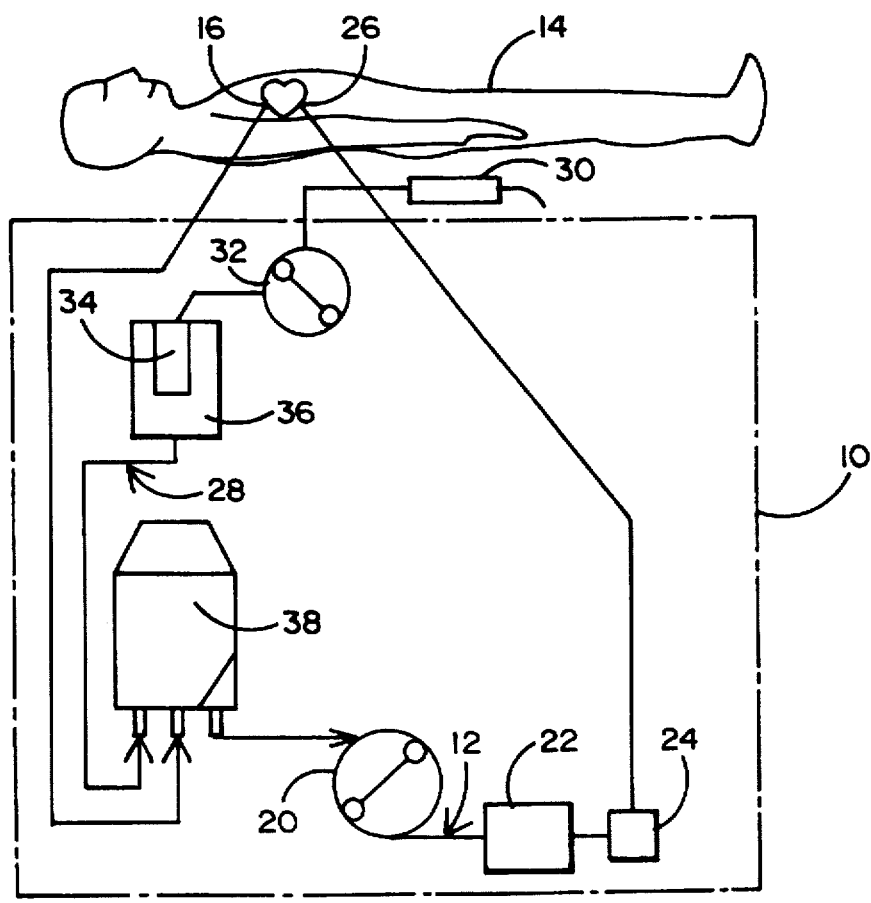
FIG. 2 schematically shows a cardiopulmonary/cardiotomy circuit modified in accordance with the invention.

As best shown in FIGS. 1 and 2, a conventional heart-lung machine 10 forms an extracorporeal cardiopulmonary circuit 12 which, in the hard shell venous/cardiotomy reservoir version of FIG. 1, diverts the blood of patient 14 from the vena cava (schematically shown at 16) into a venous/cardiotomy reservoir 18, and then pumps the blood from the reservoir 18 through pump 20, blood oxygenator 22 and arterial filter 24 into the aorta (schematically shown at 26). A cardiotomy circuit 28 runs from the cardiotomy sucker 30 through the cardiotomy pump 32 and joins the cardiopulmonary circuit 12 at the inlet to the filter/defoamer section 34 of reservoir 18.

In the soft bag venous reservoir embodiment of FIG. 2, the cardiotomy circuit 28 has its own cardiotomy reservoir 36 containing the filter-defoamer 34. The filtered and defoamed cardiotomy blood joins the venous blood in the soft bag venous reservoir 38, from which it is returned to the patient 14 through the cardiopulmonary circuit 12.

Figure 3:
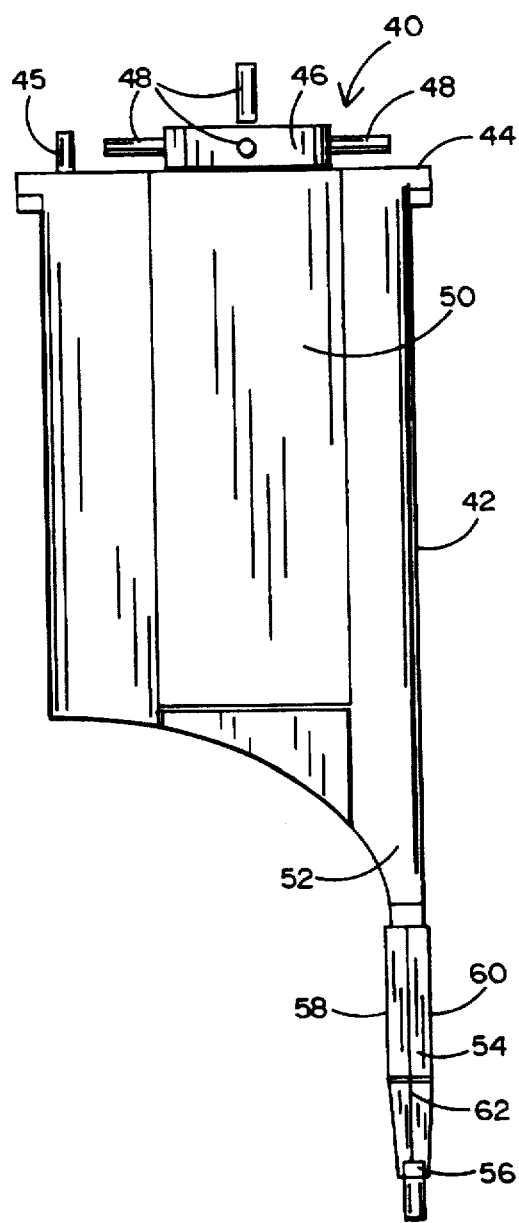
FIG. 3 is a side elevation of a soft-tipped reservoir in accordance with the invention.
Figure 4:
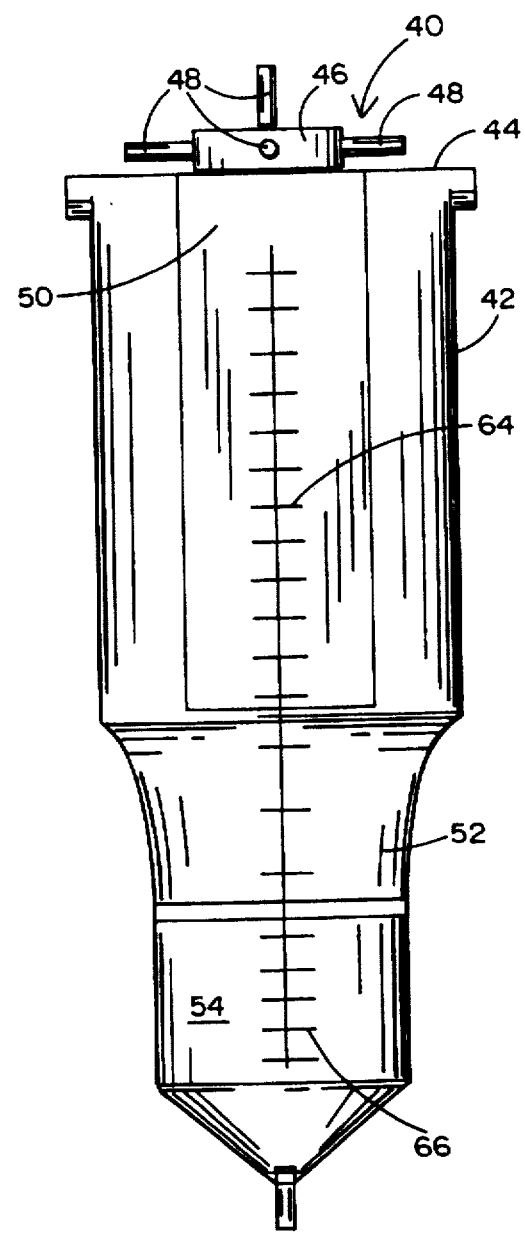
FIG. 4 is a front elevation of the reservoir of FIG. 3.

The invention combines the advantages of the embodiments of FIGS. 1 and 2 by substituting for the reservoir 18 of FIG. 1 the inventive venous/cardiotomy reservoir 40 shown (somewhat schematically) in detail in FIGS. 3 and 4. In those figures, 42 denotes the rigid housing of the reservoir 40 which is closed at its upper end by a sealed protective lid 44. A vent 45 on the lid 44 allows air to enter and exit the housing 42.

The lid 44 also carries the inlet connector manifold 46 containing the connectors 48 to which the tubes (not shown) bringing venous and cardiotomy blood to the reservoir 40 are attached. The output of the manifold 46 discharges into the filter/defoamer cartridge 50 suspended from the underside of the lid 44. The filter/defoamer 50 may be of conventional construction using layers of plastic foam and fabric to filter particulates from the blood and break up any air bubbles in it. The filtered and defoamed venous and cardiotomy blood flows into the body of housing 42 for storage.

In accordance with the invention, the bottom of the housing 42 is curved to transition into a snout 52 of elongated, narrow rectangular shape to which is attached a flexible PVC film outlet tip 54 terminating in an outlet connector 56. The outlet tip 54 is composed of a pair of flexible films 58, 60 (FIG. 3) joined at 62 to form a flat bag whose upper end is sealed to the lower end of snout 52, and which is inherently biased to sealingly collapse upon itself when it is not filled with liquid.

In a preferred embodiment, the volumetric capacity of the housing 4a is approximately 3.6 liters (>90% of the total capacity of the reservoir 40). The volumetric capacity of the outlet tip 54 is approximately 0.4 liters (<10% of total capacity). The fluid volume in the housing 42 can be accurately measured; the fluid volume in the outlet tip 54 cannot be measured as accurately. However, because the outlet tip 54 is relatively small, it will have only a minor impact on the accuracy of the overall volume measurement. Consequently, the volumetric accuracy of the reservoir 40 of this invention is sufficient for determination of the extracorporeal blood volume in a clinical setting. Liquid volume in the reservoir 40 is indicated by the graduations 64, 66 on the housing 42 and tip 54, respectively.

The curved shape of the snout 52 is important in that it provides a smooth transition for blood flow between housing 42 and tip 54 (thus minimizing blood trauma), and it allows the tip 54 to have the close proximity, essentially parallel film configuration necessary for the sealing wall collapse when the liquid is emptied. In addition, the snout shape provides an attachment zone between the housing 42 and tip 54 that is conducive to common assembly methods such as heat sealing, adhesive or solvent bonding, radio frequency welding, or mechanical fasteners.

It will be seen that the inventive reservoir preserves a volumetric accuracy sufficient for clinical measurement purposes, yet provides increased safety by preventing the introduction of air into the downstream cardiopulmonary circuit if the reservoir 40 is accidentally allowed to become empty during surgery.

An additional use of the reservoir 18 of FIG. 1 is the collection of drainage fluids from the patient's chest cavity after the patient 14 has been disconnected from the heart-lung machine 10. For this purpose, a slight vacuum is connected to the air vent (45 in FIG. 3) of the reservoir 18, the outlet of reservoir 18 is plugged, and the chest fluids drawn by the vacuum drop into the reservoir 18 where they accumulate pending disposal.

The soft venous reservoir 38 of FIG. 2 does not allow this additional use because the soft bag would collapse under a vacuum and would not be usable for storage. In the inventive reservoir 40, however, the post-operative utility of the reservoir 40 is preserved in spite of the presence of flexible tip 54 because the housing 42, which does not collapse under vacuum, retains sufficient volume to allow post-operative storage of fluids drained from the chest cavity.

It should be understood that the exemplary soft tip blood reservoir described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

I claim:

1. A blood reservoir for heart-lung machines, comprising:

a) a rigid ventable housing;

b) a blood inlet on said housing for introducing blood thereinto;

c) a flexible bag sealingly connected to the underside of said housing in fluid communication therewith, said bag being inherently biased to sealingly collapse in the absence of liquid in said bag; and d) a blood outlet on said bag on the end thereof opposite said housing for discharging blood from said housing and bag.

2. The blood reservoir of claim 1, in which said underside of said housing is tapered toward said bag so as to provide a substantially rectangular, elongated narrow interface between said housing and said bag, said bag being formed of a pair of parallel flexible films in close proximity to each other.

3. The blood reservoir of claim 2, in which said taper is so curved as to maintain a substantially uniform blood flow from said housing into said bag in order to minimize blood trauma.

4. The blood fevervoit of claim 1, in which volume indicators are provided on said housing to indicate, for given levels of blood in said housing, the volume of blood in said reservoir.

5. The blood reservoir of claim 1, in which the volumetric capacity of said bag is about 10% or less of the total capacity of said reservoir.

6. The blood reservoir of claim 1, in which the ratio of the volumetric capacity of said bag to the volumetric capacity of said housing is sufficiently small so that the volumetric accuracy of said reservoir is adequate for the determination of extracorporeal blood volume in a clinical setting.

* * * * *